US012551680B2

(12) United States Patent
Picot et al.

(10) Patent No.: US 12,551,680 B2
(45) Date of Patent: Feb. 17, 2026

(54) ROTATING LUER CONNECTOR

(71) Applicant: Becton, Dickinson and Company, Franklin Lakes, NJ (US)

(72) Inventors: John Picot, Flemington, NJ (US); Hong Zhu, Glen Rock, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 487 days.

(21) Appl. No.: 17/156,758

(22) Filed: Jan. 25, 2021

(65) Prior Publication Data

US 2021/0228857 A1 Jul. 29, 2021

Related U.S. Application Data

(60) Provisional application No. 62/966,169, filed on Jan. 27, 2020.

(51) Int. Cl.

| | |
|---|---|
| ***A61M 39/00*** | (2006.01) |
| ***A61M 39/10*** | (2006.01) |
| ***A61M 39/22*** | (2006.01) |
| *A61M 39/24* | (2006.01) |
| *A61M 39/26* | (2006.01) |

(52) U.S. Cl.

CPC ...... *A61M 39/105* (2013.01); *A61M 39/1055* (2013.01); *A61M 39/22* (2013.01); *A61M 2039/2426* (2013.01); *A61M 2039/268* (2013.01)

(58) Field of Classification Search

CPC ............ A61M 39/105; A61M 39/1055; A61M 39/22; A61M 2039/2426; A61M 2039/268; A61M 39/10; A61M 2039/1072; A61M 2039/1083; A61M 2039/0072; A61M 2039/1088; A61M 2039/1094; A61M 2039/2473; A61M 2039/1077; A61M 39/26; A61M 39/1011; A61M 2039/1033; A61M 2039/1061; A61M 16/04; A61M 16/0816; A61M 39/00; A61M 39/223;

(Continued)

(56) References Cited

U.S. PATENT DOCUMENTS 9,913,971 B2 * 3/2018 Ogawa ................ A61M 39/045
9,970,794 B2 5/2018 DeKalb (Continued)

FOREIGN PATENT DOCUMENTS

JP 3761854 B2 1/2006
JP 2006345916 A 12/2006

(Continued)

*Primary Examiner* — Rebecca E Eisenberg
(74) *Attorney, Agent, or Firm* — The Webb Law Firm

(57) ABSTRACT

A medical connector includes a body, a first connector defining a longitudinal axis extending from a first end of the first connector to a second end of the first connector and a second connector secured to the body and in fluid communication with the first connector. The first connector is secured to and rotatable relative to the body about the longitudinal axis. The first connector includes a valve member and is configured to be secured to a syringe barrel. The valve member of the first connector having a sealed position and an open position. The valve member of the first connector is configured to move from the sealed position to the open position when a syringe barrel is secured to the first connector.

17 Claims, 7 Drawing Sheets

(58) Field of Classification Search
CPC ...... A61M 2039/229; A61M 2039/267; A61B 1/01; A61B 1/018; A61B 1/2676
See application file for complete search history.

(56) References Cited

U.S. PATENT DOCUMENTS

| | | | | |
|---|---|---|---|---|
| 2004/0171993 | A1* | 9/2004 | Bonaldo | A61M 39/26 604/248 |
| 2012/0029479 | A1* | 2/2012 | Kraushaar | A61M 39/105 604/533 |
| 2015/0335228 | A1* | 11/2015 | Lei | A61B 1/01 600/109 |
| 2016/0296740 | A1* | 10/2016 | Adams | A61M 39/10 |
| 2017/0036007 | A1* | 2/2017 | Hallisey | A61M 39/26 |
| 2019/0282794 | A1* | 9/2019 | Carlsson | A61M 39/1011 |
| 2019/0366038 | A1* | 12/2019 | Denman | A61M 27/008 |
| 2019/0366052 | A1* | 12/2019 | Burkholz | A61M 39/1055 |
| 2019/0388674 | A1* | 12/2019 | Sasahara | A61M 39/105 |
| 2020/0345996 | A1* | 11/2020 | DeMeritt | A61M 39/1011 |
| 2021/0178080 | A1* | 6/2021 | Shetty | A61M 39/10 |

FOREIGN PATENT DOCUMENTS

| | | | |
|---|---|---|---|
| JP | 2007244776 | A | 9/2007 |
| JP | 2012523300 | A | 10/2012 |
| JP | 2014128682 | A | 7/2014 |
| JP | 2016540618 | A | 12/2016 |
| JP | 3212189 | U | 8/2017 |
| WO | 2015074044 | A1 | 5/2015 |

* cited by examiner

ROTATING LUER CONNECTOR

CROSS-REFERENCE TO RELATED APPLICATION

The present application claims priority to U.S. Provisional Application Ser. No. 62/966,169, filed Jan. 27, 2020, and entitled "Rotating Luer Connector", the entire disclosure of which is hereby incorporated by reference in its entirety.

BACKGROUND OF THE INVENTION

Field of the Disclosure

The present application relates generally to a medical connector and, more specifically, a rotating luer connector.

Description of the Related Art

Luer connections on medical connectors include luer lock threads that cooperate with corresponding threads of a mating component, such as a syringe. The standards governing luer connections, such as ISO 80369-7, do not standardize the thread timing position. Accordingly, when a syringe is secured to a luer connector, graduation or other markings on a barrel of the syringe may not be oriented in a position to allow a healthcare professional to read the graduation markings.

SUMMARY OF THE INVENTION

In one aspect, a medical connector includes a body, a first connector defining a longitudinal axis extending from a first end of the first connector to a second end of the first connector, with the first connector secured to and rotatable relative to the body about the longitudinal axis. The first connector includes a valve member and is configured to be secured to a syringe barrel, with the valve member of the first connector having a sealed position and an open position. The valve member of the first connector is configured to move from the sealed position to the open position when a syringe barrel is secured to the first connector. The medical connector also includes a second connector secured to the body and in fluid communication with the first connector.

The first connector may have a predetermined angle of rotation about the longitudinal axis, where the predetermined angle of rotation is less than 360 degrees. The predetermined angle of rotation may be 45 degrees. The first connector member may include a stop configured to restrict the first connection member to the predetermined angle of rotation.

The medical connector may include a third connector secured to the body and in fluid communication with the first and second connectors. The second connector may be a female luer member, and the third connector may be a male luer member.

The first connector may include a dial member and a connector body, with the dial member including a projection configured to be engaged by a person to rotate the first connector about the longitudinal axis. The connector body may include an external thread and may be configured to receive a male luer connector of a syringe barrel.

The valve member may be an elastomeric sleeve defining a slit, with the slit configured to be closed when the valve member is in the sealed position and open when the valve member is in the open position. The valve member may be received by a sleeve housing, with the sleeve housing positioned within an internal space defined by the dial member and the connector body. The body may include a main portion, an inner flow portion, and an outer hub portion, with the inner flow portion received by an internal space defined by the outer hub portion, and with the first connector secured to and rotatable relative to the outer hub portion. The inner flow portion may define an opening in fluid communication with the second connector.

BRIEF DESCRIPTION OF THE DRAWINGS

The above-mentioned and other features and advantages of this disclosure, and the manner of attaining them, will become more apparent and the disclosure itself will be better understood by reference to the following descriptions of aspects of the disclosure taken in conjunction with the accompanying drawings, wherein.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

Figure 1:
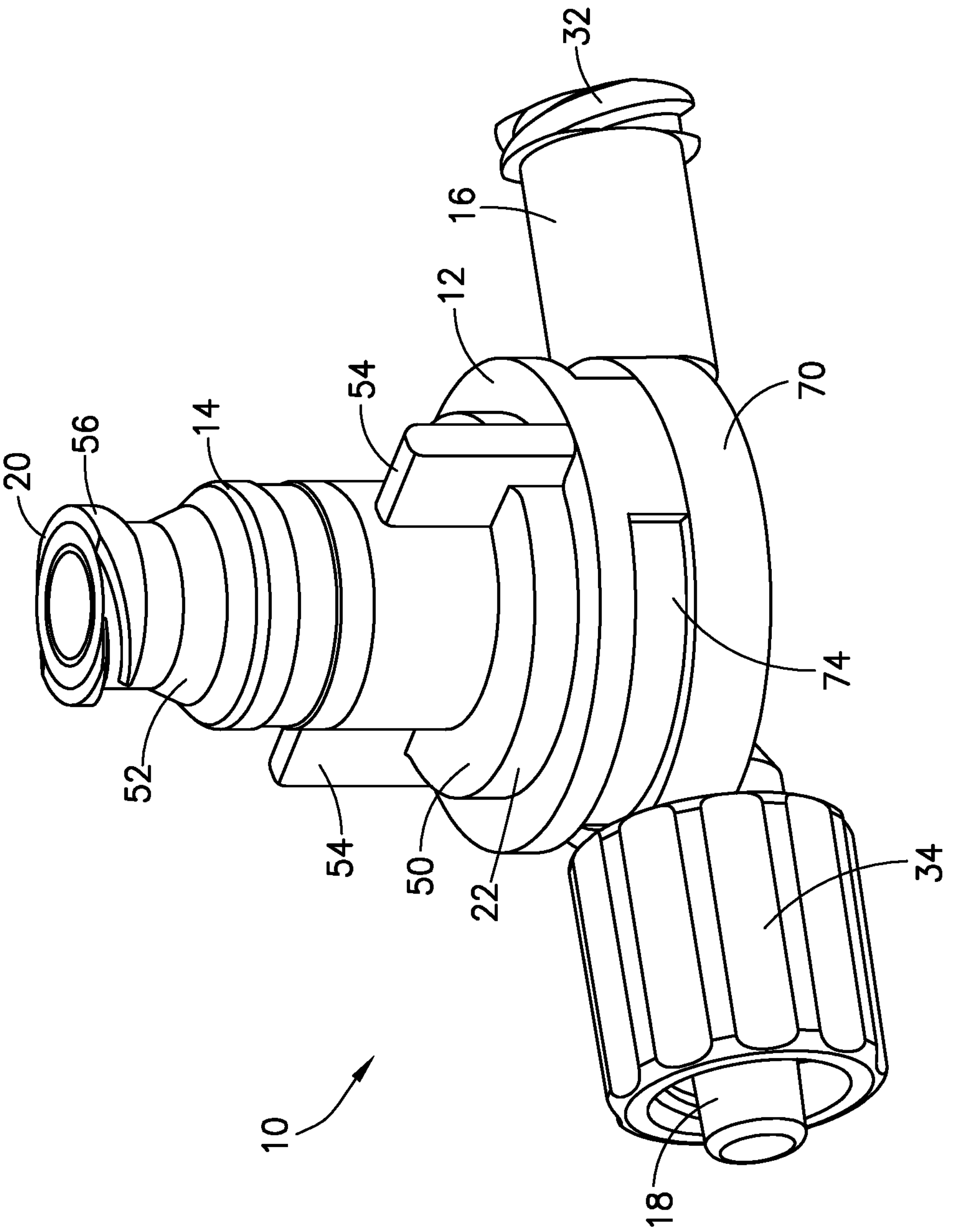
FIG. 1 is a perspective view of a medical connector according to one aspect or embodiment of the present application.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention.

Hence, specific dimensions and other physical characteristics related to the aspects disclosed herein are not to be considered as limiting. All numbers and ranges used in the specification and claims are to be understood as being modified in all instances by the term "about". By "about" is meant plus or minus twenty-five percent of the stated value, such as plus or minus ten percent of the stated value. However, this should not be considered as limiting to any analysis of the values under the doctrine of equivalents.

Unless otherwise indicated, all ranges or ratios disclosed herein are to be understood to encompass the beginning and ending values and any and all subranges or subratios subsumed therein. For example, a stated range or ratio of "1 to 10" should be considered to include any and all subranges or subratios between (and inclusive of) the minimum value of 1 and the maximum value of 10; that is, all subranges or subratios beginning with a minimum value of 1 or more and ending with a maximum value of 10 or less. The ranges and/or ratios disclosed herein represent the average values over the specified range and/or ratio.

The terms "first", "second", and the like are not intended to refer to any particular order or chronology, but refer to different conditions, properties, or elements.

Figure 7:
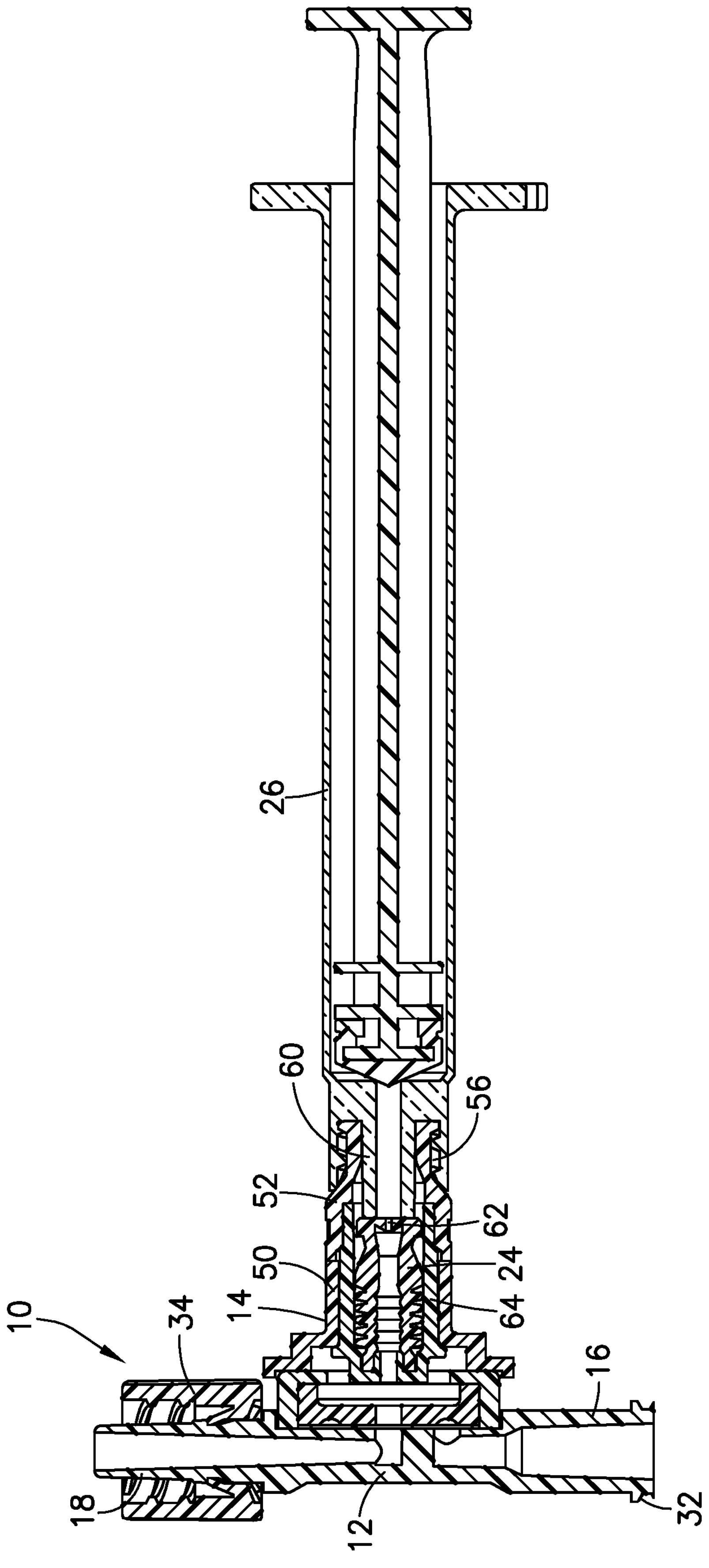
FIG. 7 is a cross-sectional view taken along line 7-7 in FIG. 6.

Referring to FIGS. 1-9, a medical connector 10 according to one aspect or embodiment of the present application includes a body 12, a first connector 14, a second connector 16, and a third connector 18. The first connector 14 defines a longitudinal axis L extending from a first end 20 of the first connector 14 to a second end 22 of the first connector 14. The first connector 14 is secured to and rotatable relative to the body 12 about the longitudinal axis L. The first connector 14 includes a valve member 24 and is configured to be secured to a syringe barrel 26, as shown in FIGS. 6-9. The valve member 24 of the first connector 14 has a sealed position and an open position. The valve member 24 of the first connector 14 is configured to move from the sealed position to the open position when the syringe barrel 26 is secured to the first connector 14, as shown in FIG. 7. The second connector 16 is secured to the body 12 and is in fluid communication with the first connector 14. The third connector 18 secured to the body 12 and is in fluid communication with the first and second connectors 14,16.

Figure 4:
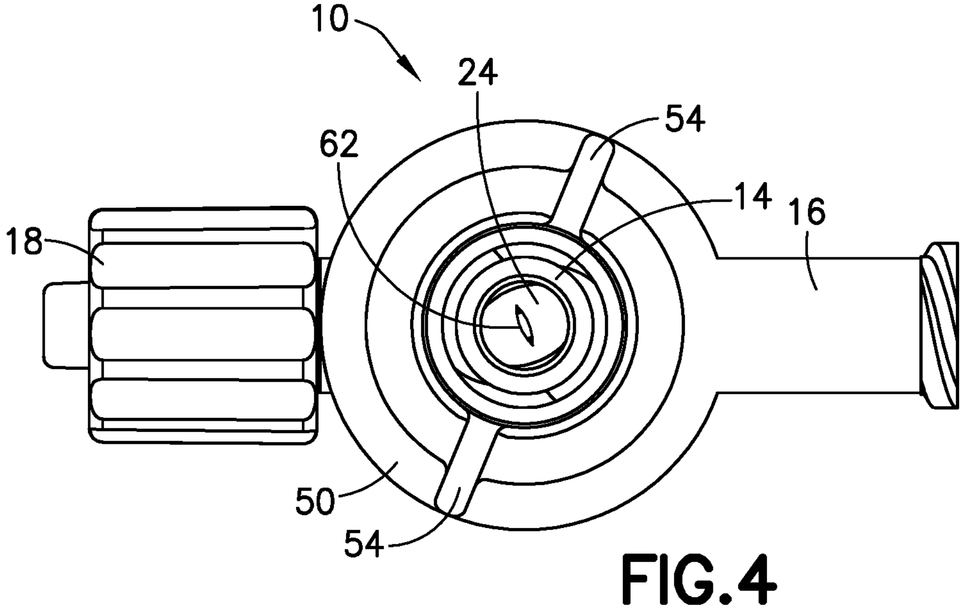
FIG. 4 is a top view of the medical connector of FIG. 1, showing a first rotational position of the medical connector.
Figure 5:
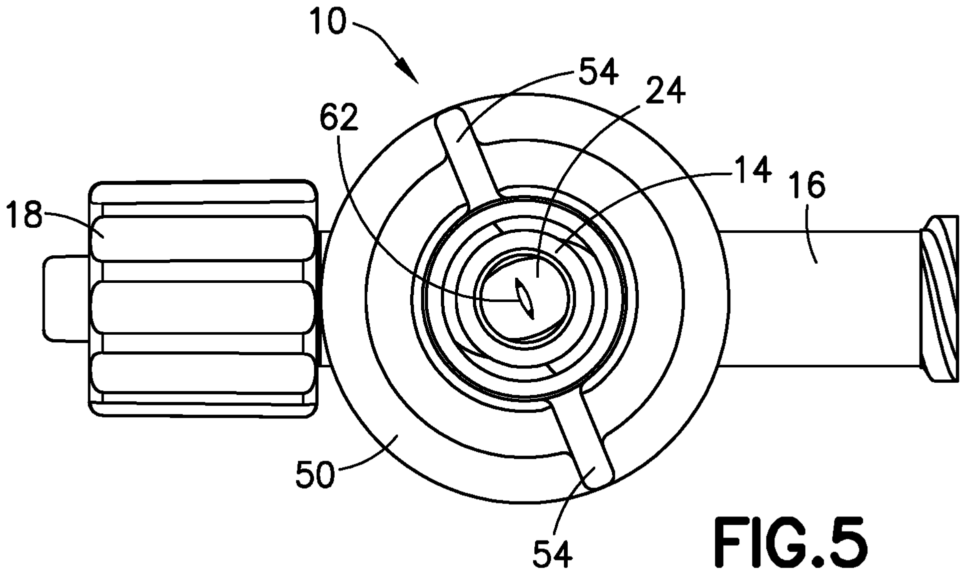
FIG. 5 is a top view of the medical connector of FIG. 1, showing a second rotational position of the medical connector.
Figure 6:
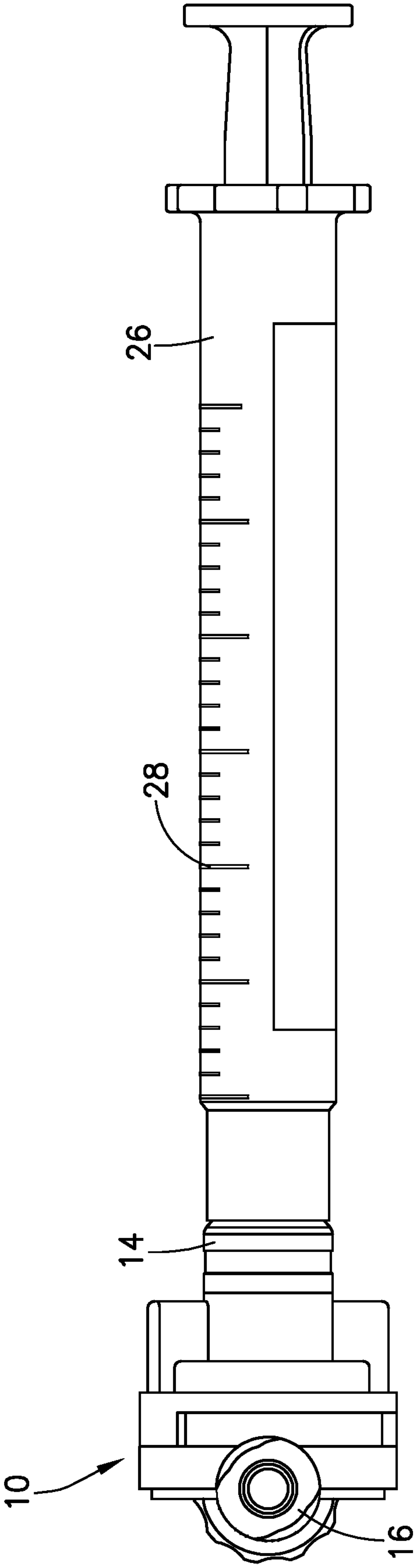
FIG. 6 is a front view of the medical connector of FIG. 1, showing the medical connector secured to a syringe barrel.

As discussed in more detail below, the first connector 14 is rotatable relative to the body 12 about the longitudinal axis L between a first rotational position, shown in FIGS. 4 and 8, and a second rotational position, shown in FIGS. 5 and 9. When the syringe barrel 26 is secured to the first connector 14, the rotation of the first connector 14 relative to the body 12 allows the syringe barrel 26 to also be rotated to change an orientation of graduation markings 28 on the syringe barrel 26 thereby facilitating visualization of the graduation markings 28 by a healthcare professional. The medical connector 10 may be utilized in connection with or integrated with a flow sensor system, such as the flow sensor system disclosed in U.S. Pat. No. 9,970,794, which is hereby incorporated by reference in its entirety.

Figure 3:
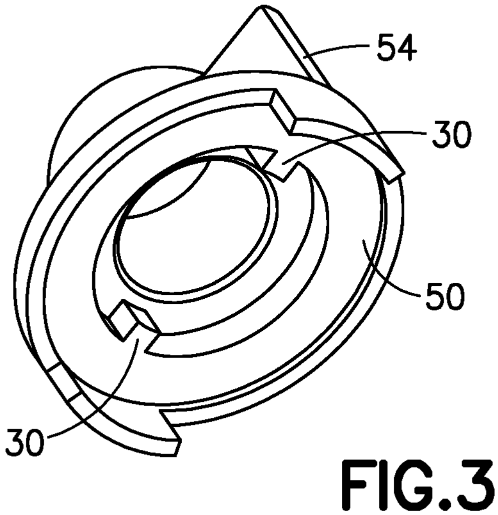
FIG. 3 is a bottom view of a dial member of the medical connector of FIG. 1.

In one aspect or embodiment, the first connector 14 has a predetermined angle of rotation about the longitudinal axis L. The predetermined angle of rotation may be less than 360 degrees. The predetermined angle of rotation may be 45 degrees. As shown in FIG. 3, the first connector member 14 may include a stop 30 configured to restrict the first connection member 14 to the predetermined angle of rotation. The stop 30 may engage corresponding structure on the body 12 to limit the predetermined angle of rotation, although other suitable arrangements may be utilized.

Referring again to FIGS. 1-9, the second connector 16 is a female luer member with external threads 32 and the third connector 18 is a male luer member with a rotating luer lock 34, although other suitable connection arrangements may be utilized. The first connector 14 includes a dial member 50 and a connector body 52. The connector body 52 may be secured to the connector body 52 or formed integrally with the connector body 52. The dial member 50 includes a pair of projections 54 configured to be engaged by a healthcare professional to rotate the first connector 14 about the longitudinal axis L, although one or more projections 54 may be provided. The connector body 52 includes an external thread 56 and is configured to receive a male luer connector 60 of the syringe barrel 26. The valve member 24 is an elastomeric sleeve defining a slit 62, although other suitable arrangements may be utilized. The slit 62 is configured to be closed when the valve member 24 is in the sealed position and open when the valve member 24 is in the open position. As shown in FIG. 7, the male luer connector 60 of the syringe barrel 26 engages and compresses the valve member 24 as the syringe barrel 26 is secured to the first connector 14 by rotating the syringe barrel 26 relative to the first connector 14. The compression of the valve member 24 deforms the valve member 24 and opens the slit 62. The valve member 24 is received by a sleeve housing 64. The sleeve housing 64 is positioned within an internal space 66 defined by the dial member 50 and the connector body 52. The sleeve housing 64 is secured to a portion of the valve member 24, with the sleeve housing 64 secured to the dial member 50 and the connector body 52.

Figure 2:
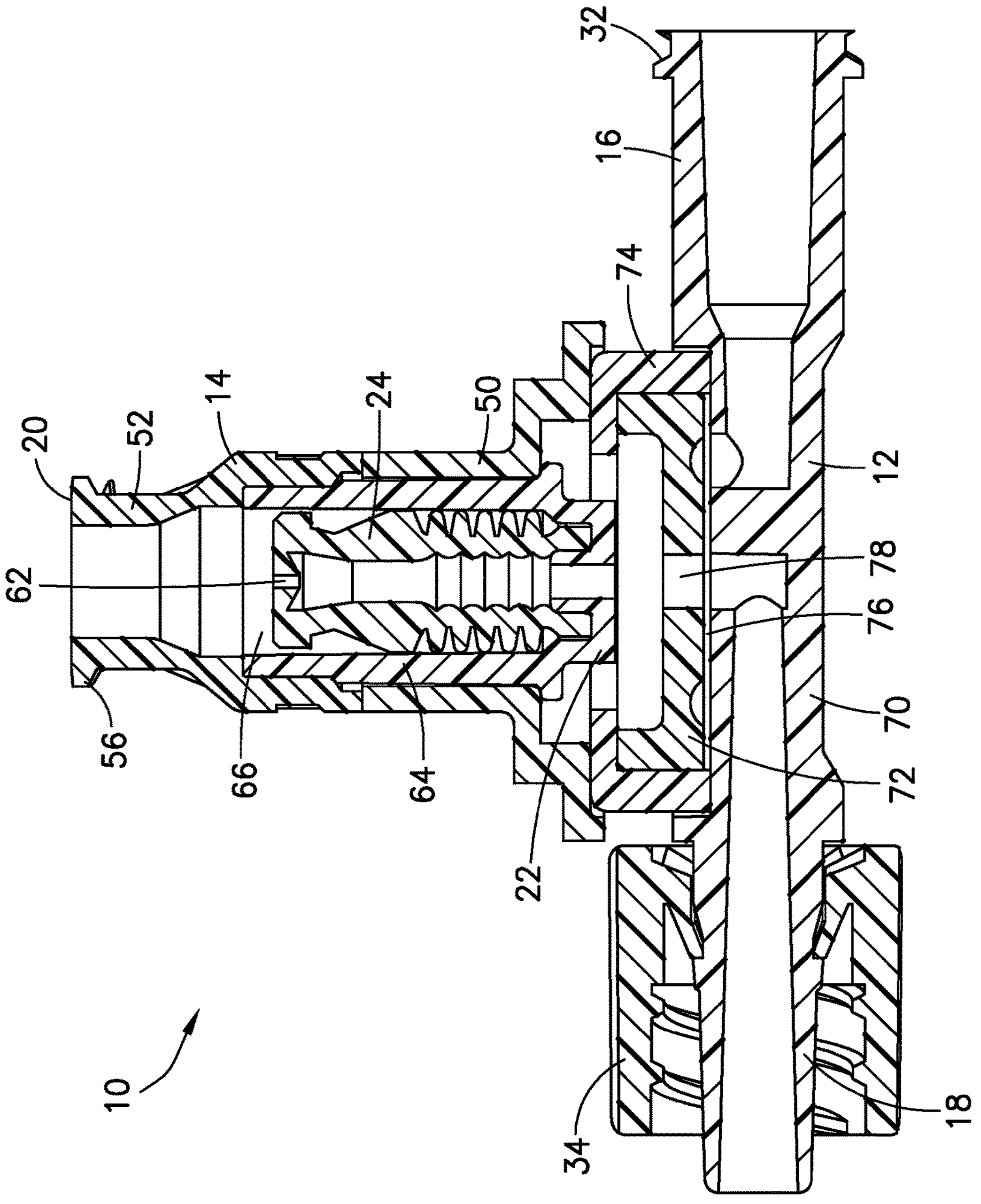
FIG. 2 is a cross-sectional view taken along line 2-2 in FIG. 2.

Referring to FIGS. 1 and 2, the body 12 of the medical connector 10 includes a main portion 70, an inner flow portion 72, and an outer hub portion 74. The inner flow portion 72 is received by an internal space 76 defined by the outer hub portion 74, with the first connector 14 secured to and rotatable relative to the outer hub portion 74. The inner flow portion 72 defines an opening 78 in fluid communication with the second connector 16. The main portion 70, inner flow portion 72, and outer hub portion 74 may be formed integrally with each other or may be separately formed and secured to each other. The dial member 50 of the first connector 14 engages the outer hub portion 74 and is rotatable relative to the outer hub portion 74. The dial member 50 forms a sealed interface with the outer hub portion 74. Although not shown, a seal, such as an O-ring, may be provided to form the sealed interface between the dial member 50 and the outer hub portion 74.

The first connector 14 may further include a ratchet arrangement (not shown) to provide audible and/or tactile feedback during rotation of the first connector 14. The first connector 14 may also include a torsion spring (not shown) to bias the first connector 14 to the first rotational position or the second rotational position. Further, the first connector 14 may include a torque limiter (not shown) to prevent damage to the first connector 14 if a predetermined torque is applied to the first connector 14 after abutting the stop 30.

Figure 8:
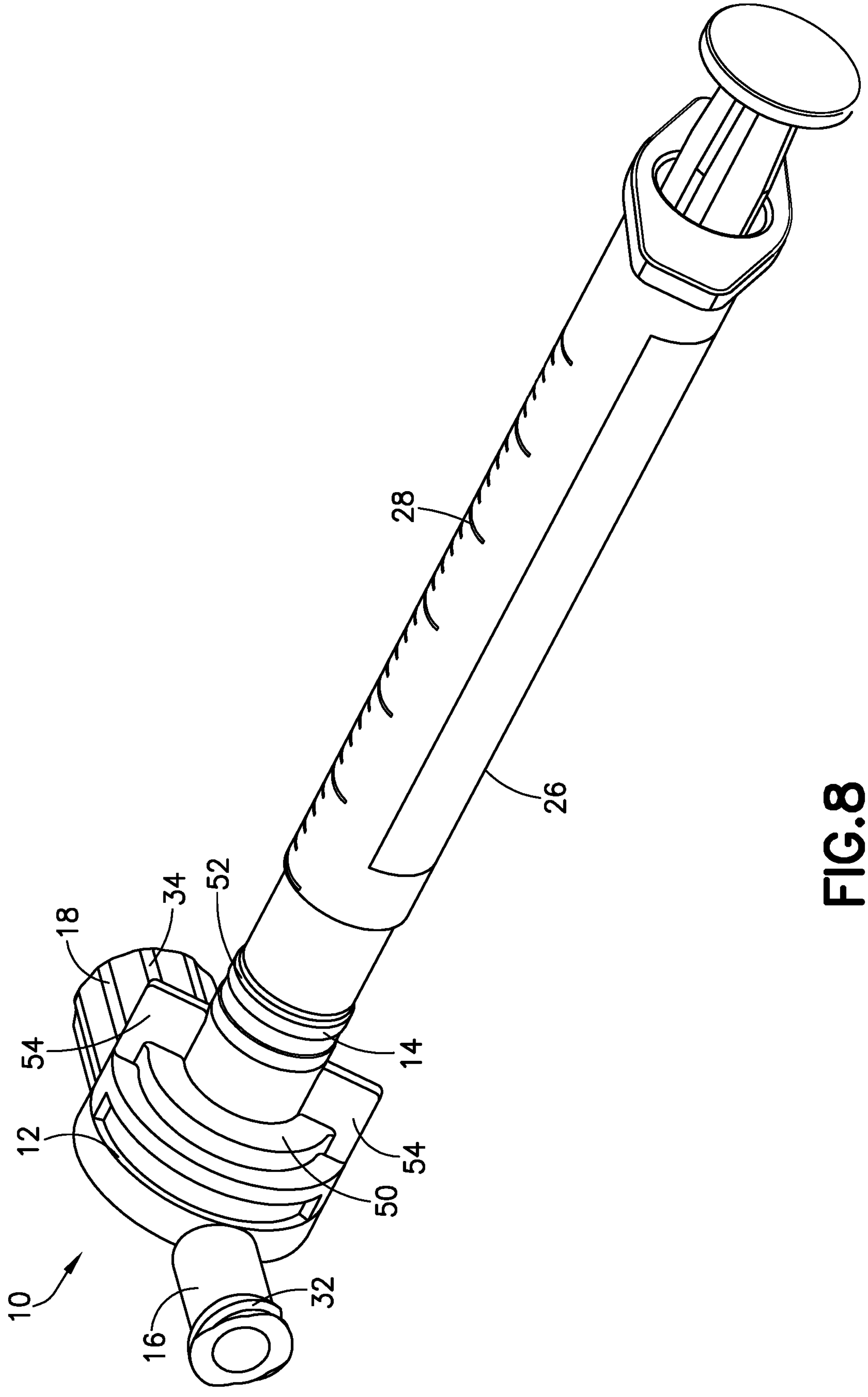
FIG. 8 is a perspective view of the medical connector of FIG. 1, showing the medical connector secured to a syringe barrel with the medical connector in a first rotational position.
Figure 9:
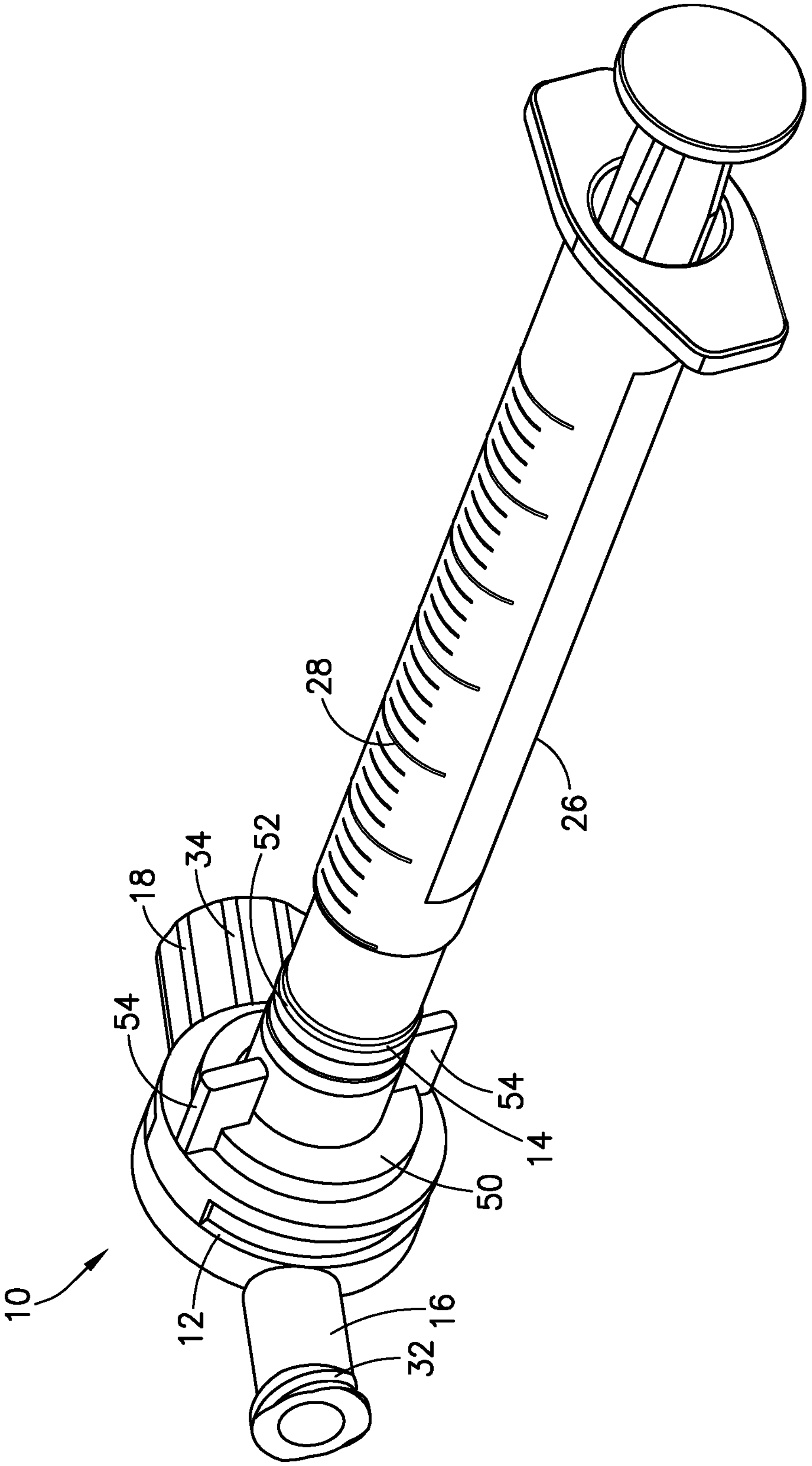
FIG. 9 is a perspective view of the medical connector of FIG. 1, showing the medical connector secured to a syringe barrel with the medical connector in a second rotational position.

Referring to FIGS. 8 and 9, according to one aspect or embodiment of the present application, the syringe barrel 26 is secured to the medical connector 10 by inserting the male luer 60 of the syringe barrel 26 into the connector body 52 of the first connector 14 and rotating the syringe barrel 26 clockwise relative to the medical connector 10 until the mating threads of the connector body 52 and the male luer 60 are fully engaged. In one aspect or embodiment, the syringe barrel 26 is rotated relative to the first connector 14 180 degrees until the mating threads have sufficient engagement or friction and further rotating the syringe barrel 26 and the first connector 14 together 45 degrees such that the first connector 14 is in the first rotational position. With the syringe barrel 26 secured to the medical connector 10 and the first connector 14 in the first rotational position, as shown in FIG. 8, a healthcare professional may rotate the first connector 14 and syringe barrel 26 from 0 to 45 degrees in a counterclockwise direction to orient the graduation markings 28 on the syringe barrel 26 to allow visualization of the graduation markings 28 as needed. The syringe barrel 26 may be disconnected from the medical connector 10 by rotating the syringe barrel 26 and the first connector 14 together in the counterclockwise direction until the syringe barrel 26 and first connector 14 are in the second rotational positon, as shown in FIG. 9, and then rotating the syringe barrel 26 relative to the first connector 14 to separate the syringe barrel 26 from the first connector 14.

In one aspect or embodiment, the first connector 14 is rotatable 360 degrees and does not include any stops or structure to limit rotation. The dial member 50 is grasped by a healthcare professional to secure and remove the syringe barrel 26 from the first connector 14 of the medical connector 10.

While this disclosure has been described as having exemplary designs, the present disclosure can be further modified within the spirit and scope of this disclosure. This application is therefore intended to cover any variations, uses, or adaptations of the disclosure using its general principles. To the extent possible, one or more features of any embodiment or aspect can be combined with one or more features of any other embodiment or aspect. Further, this application is intended to cover such departures from the present disclosure as come within known or customary practice in the art to which this disclosure pertains and which fall within the limits of the appended claims.

What is claimed is:

1. A medical connector comprising:

a body;

a first connector defining a longitudinal axis extending from a first end of the first connector to a second end of the first connector, the first end configured to receive a luer connector of a syringe barrel and the second end secured to and rotatable relative to the body by a predetermined angle of rotation greater than 45 degrees and less than 360 degrees about the longitudinal axis, the first connector comprising a valve member having a sealed position and an open position, the valve member of the first connector configured to move from the sealed position to the open position when a syringe barrel is secured to the first connector, wherein the first connector further comprises a dial member and a connector body, with the dial member offset from the connector body in a longitudinal direction such that the connector body is positioned at the first end and the dial member is positioned at the second end, with the dial member including:

a stop rotatably engaging a structure on the body to restrict the rotation of the second end to the predetermined angle of rotation; and one or more projections configured to be engaged by a person;

wherein rotation of the first connector relative to the body about the longitudinal axis is facilitated by engagement with the one or more projections by the person; and a second connector secured to the body and in fluid communication with the first connector.

2. The medical connector of claim 1, further comprising a third connector secured to the body and in fluid communication with the first and second connectors.

3. The medical connector of claim 2, wherein the second connector comprises a female luer member, and wherein the third connector comprises a male luer member.

4. The medical connector of claim 1, wherein each of the one or more projections comprises an elongate member extending in the longitudinal direction and protruding radially out from the dial member, with flat opposing front and rear surfaces configured to be engaged by the person to rotate the first connector about the longitudinal axis.

5. The medical connector of claim 4, wherein the first end of the connector body comprises an external thread and is configured to receive a male luer connector of a syringe barrel.

6. The medical connector of claim 4, wherein the valve member comprises an elastomeric sleeve defining a slit, the slit is configured to be closed when the valve member is in the sealed position and open when the valve member is in the open position.

7. The medical connector of claim 6, wherein the valve member is received by a sleeve housing, the sleeve housing positioned within an internal space defined by the dial member and the connector body.

8. The medical connector of claim 1, wherein the body comprising a main portion, an inner flow portion, and an outer hub portion, the inner flow portion received by an internal space defined by the outer hub portion, the first connector secured to and rotatable relative to the outer hub portion.

9. The medical connector of claim 8, wherein the inner flow portion defines an opening in fluid communication with the second connector.

10. The medical connector of claim 1, wherein rotation of the first connector relative to the body reorients the syringe barrel relative to the body when the syringe barrel is secured to the first connector.

11. The medical connector of claim 1, wherein the valve member is uncompressed when the first connector is in the sealed position, and wherein the valve member is compressed when the first connector is in the open position.

12. The medical connector of claim 1, wherein rotation of the first connector relative to the body orients graduation markings on the syringe barrel to allow visualization of the graduation markings.

13. The medical connector of claim 1, wherein the first connector and the second connector are secured to the body such that the first connector is orthogonal to the second connector.

14. The medical connector of claim 1, wherein rotation of the first connector relative to the body reorients the syringe barrel relative to the body without affecting fluid flow through the first connector into the body.

15. A fluid delivery assembly, comprising:

the medical connector of claim 1; and the syringe barrel with the luer connector, wherein the luer connector of the syringe barrel is inserted into the first end of the first connector.

16. The fluid delivery assembly of claim 15, wherein rotation of the first connector relative to the body reorients the syringe barrel relative to the body without affecting fluid flow through the first connector into the body.

17. The fluid delivery assembly of claim 15, wherein rotation of the first connector relative to the body orients graduation markings on the syringe barrel to allow visualization of the graduation markings.

* * * * *